US012521165B2

(12) United States Patent
Miri et al.

(10) Patent No.: US 12,521,165 B2
(45) Date of Patent: Jan. 13, 2026

(54) SYSTEMS AND METHODS FOR HYBRID PERISTALTIC PUMP FLOW

(71) Applicant: Medtronic Navigation, Inc., Louisville, CO (US)

(72) Inventors: Mohammad Miri, Longmont, CO (US); Matthew S. Palm, Black Hawk, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 483 days.

(21) Appl. No.: 18/080,808

(22) Filed: Dec. 14, 2022

(65) Prior Publication Data

US 2024/0197384 A1 Jun. 20, 2024

(51) Int. Cl.
*A61B 18/14* (2006.01)

(52) U.S. Cl.
CPC ........ *A61B 18/14* (2013.01); *A61B 2218/002* (2013.01)

(58) Field of Classification Search
CPC .......................... A61B 18/14; A61B 2218/002
USPC ............................................................ 606/32
See application file for complete search history.

(56) References Cited

U.S. PATENT DOCUMENTS 8,790,303 B2 7/2014 Williams et al.
2007/0258838 A1* 11/2007 Drake ................ F04B 43/0072 417/477.2
2012/0305129 A1* 12/2012 Austin ................ F04B 43/1292 141/237
2013/0267894 A1* 10/2013 Woolford ............. A61B 18/148 604/67
2015/0157386 A1* 6/2015 Bloom ............... A61B 18/1206 606/34
2016/0287779 A1* 10/2016 Orczy-Timko ..... A61M 3/0202
2017/0184088 A1* 6/2017 Macari ................ F04B 43/1292
2018/0369458 A1* 12/2018 Mangual-Soto ... A61B 18/1492
2019/0290811 A1 9/2019 Bono et al.
2020/0188014 A1* 6/2020 Woloszko ............. A61B 18/16

OTHER PUBLICATIONS

PCT/IB2023/062269 PCT Search Report and Written Opinion dated Mar. 5, 2024, 18 pages.

* cited by examiner

*Primary Examiner* — Linda C Dvorak
(74) *Attorney, Agent, or Firm* — Husch Blackwell LLP

(57) ABSTRACT

Systems and methods whereby an electrosurgical device provides electrosurgical treatment to a tissue area while offering simultaneous irrigation and suction capabilities. A hybrid pump attachment including a plurality of flexible tubes is fluidly connectable to the electrosurgical device, wherein the plurality of flexible tubes is orientated within the hybrid pump attachment such that, when attached to the peristaltic pump, the plurality of tubes at least partially surrounds a rotor and a plurality of rollers of the peristaltic pump. The rotor is rotatable about a central axis such that the plurality of rollers conveys fluid through the plurality of flexible tubes by way of applying intermittent forces on the external surface of the plurality of flexible tubes, wherein at least a first tube conveys a first fluid to a first location and at least a second tube conveys a second fluid to a second location.

18 Claims, 5 Drawing Sheets

SYSTEMS AND METHODS FOR HYBRID PERISTALTIC PUMP FLOW

FIELD

The present technology is generally related to instruments or tools used in performing surgery on a patient and, more particularly, to a peristaltic pump attachment for simultaneous suction and irrigation during electrosurgical procedures.

BACKGROUND

Electrosurgery includes such techniques as cutting, coagulation, hemostasis, and/or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by the surgeon and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Cutting and coagulation are often performed with electrodes in the monopolar arrangement while hemostasis is performed with electrodes in the bipolar arrangement. Historically, two distinct electrosurgical devices, one monopolar and the other bipolar, were used to perform different functions in surgery, such as tissue cutting and coagulating and tissue sealing. Some electrosurgical devices capable of performing multiple techniques such as cutting and coagulating tissue or cutting, coagulating, and sealing tissue, including fluid-assisted sealing of tissue, have been developed.

Fluid-assisted electrosurgical devices apply radiofrequency (RF) electrical energy and electrically conductive fluid to provide for sealing of soft tissues and bone in applications of orthopedics (such as total hip arthroplasty, or THA, and total knee arthroplasty, or TKA), spinal oncology, neurosurgery, thoracic surgery, and cardiac implantable electronic devices as well as others such as general surgery within the human body. The combination of RF energy and the electrically conductive fluid permits the electrosurgical device to operate at approximately 100 degrees Celsius, which is nearly 200 degrees Celsius less than traditional electrosurgical devices. Typically, hemostasis is performed with fluid-assisted devices having electrodes in the bipolar arrangement that are referred to as bipolar sealers. By controlling bleeding, bipolar sealers have been demonstrated to reduce the incidence of hematoma and transfusions, help maintain hemoglobin levels, and reduce surgical time in a number of procedures, and may reduce the use of hemostatic agents.

Peristaltic pumps have been widely utilized in medical devices, such as fluid-assisted electrosurgical devices, to irrigate the fluid. Peristaltic pumps are generally used because the fluid transfer can occur without any part of the pump coming in contact with the liquid. Peristaltic pumps typically have two or more rollers but may have other configurations. The rollers are generally spaced circumferentially evenly apart and are mounted on a rotating carrier that moves the rollers in a circle. A flexible tube needs to be placed inside the pump in the tube channel, which may be relatively soft and pliable so the rollers may rotate in a circular movement and compress the tubing against the wall, squeezing the fluid through the tubing ahead of the rollers. The rollers are configured to almost completely occlude the tubing, and operate essentially as a positive displacement pump, wherein each passage of a roller through the semi-circle pumps the entire volume of the fluid contained in the tubing segment between the rollers. Some of these pumps may come with the flexible tube already installed and some may require the placement of the tube inside the pump. For those with the tube already placed inside the pump, it is important to connect the source and destination of the fluid to the correct port and for the others, it is important to place the tube in the correct orientation inside the pump.

Conventionally, a single pump with a single tube has been utilized to provide fluid to these electrosurgical devices. These systems merely allow for a single fluid or composition of fluids to flow in a single direction and have limited operability. While some pumps may utilize more than a single tube, the directional flow of fluid remains limited to a single direction, either to or from a single source due to the reliance of a single pump. In an attempt to compensate for these limitations, some systems have implemented multiple pumps for additional fluid control.

Thus, there is a present need for improved electrosurgical technology, particularly to reduce the number of components in fluid pumping mechanisms while integrating multi-directional fluid flow.

SUMMARY

The techniques of this disclosure generally relate to hybrid suction and irrigation peristaltic pumps.

In one aspect, the present disclosure provides a system for electrosurgical treatment comprising an electrosurgical device configured to provide electrosurgical treatment to a tissue area and a peristaltic pump including a rotor and a plurality of rollers, wherein the rotor and the plurality of rollers have a central axis. In embodiments, a hybrid pump attachment may include a plurality of flexible tubes fluidly connectable to the electrosurgical device, wherein the plurality of flexible tubes is orientated within the hybrid pump attachment such that when the hybrid pump attachment is integrated with the peristaltic pump, the plurality of flexible tubes at least partially surrounds the rotor and the plurality of rollers, wherein the plurality of rollers aligns with the plurality of tubes. The rotor may be rotatable about the central axis, wherein the plurality of rollers convey fluid through the plurality of flexible tubes by way of applying intermittent forces on the external surface of the plurality of flexible tubes, wherein at least a first tube of the plurality of tubes conveys a first fluid to a first location and at least a second tube of the plurality of tubes conveys a second fluid to a second location.

In one aspect, the present disclosure provides a hybrid pump attachment comprising a casing including a plurality of flexible tubes configured to be integrated with a peristaltic pump. The plurality of flexible tubes orientated within the casing and fluidly attachable to at least one of a fluid source, an electrosurgical device, and a waste destination, wherein a plurality of rollers integrated with the peristaltic pump conveys fluid through the plurality of flexible tubes by way of applying intermittent forces on the external surface of the plurality of flexible tubes as the plurality of rollers rotate about an axis within the peristaltic pump, wherein at least a first tube of the plurality of flexible tubes conveys a first fluid to a first location and at least a second tube of the plurality of flexible tubes conveys a second fluid to a second location.

In one aspect, the present disclosure provides a method for use with an electrosurgical device, the method comprising providing an electrosurgical treatment to a tissue area via an electrosurgical device. Irrigating, through a first flexible tube, a first fluid from a source and applying the first fluid to the tissue area with the electrosurgical device during the electrosurgical treatment and suctioning, through a second flexible tube, a second fluid from the tissue area to a target destination with the electrosurgical device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Subject matter hereof may be more completely understood in circumstances of the following detailed description of various embodiments in connection with the accompanying figures, in which.

Figure 1:
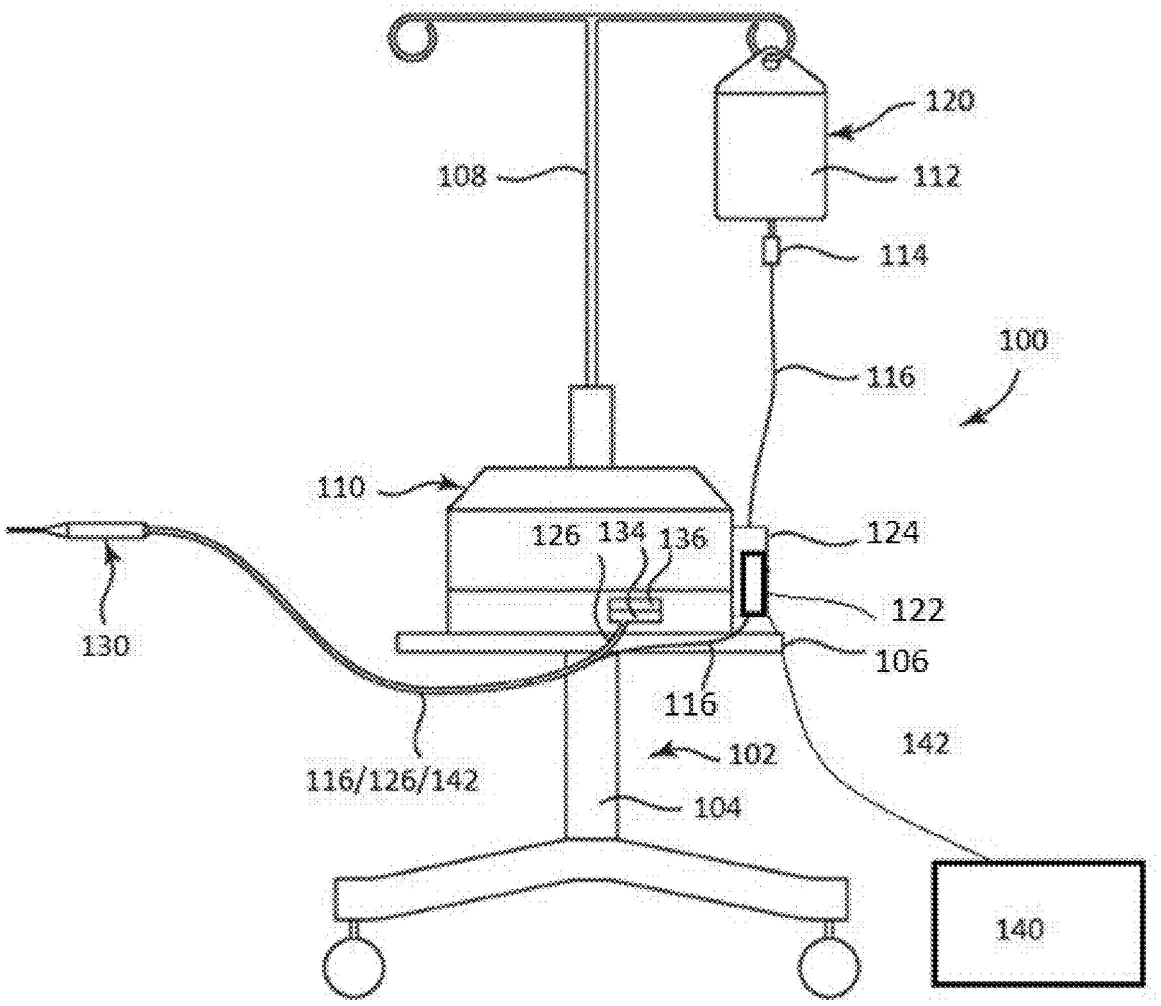
FIG. 1 depicts a front view illustrating an embodiment of a system according to the present disclosure including an example electrosurgical unit in combination with a fluid source, an example handheld electrosurgical device and a peristaltic pump with an integrated hybrid peristaltic pump attachment, according to embodiments.

While various embodiments are amenable to various modifications and alternative forms, specifics thereof have been shown by way of example in the drawings and will be described in detail. It should be understood, however, that the intention is not to limit the claimed disclosure to the particular embodiments described. On the contrary, the intention is to cover all modifications, equivalents, and alternatives falling within the spirit and scope of the subject matter as defined by the claims.

DETAILED DESCRIPTION

Reference now will be made in detail to embodiments of the disclosure, one or more examples of which are illustrated in the drawings. Each example is provided by way of explanation in the disclosure and is not limited thereto. In fact, it will be apparent to those skilled in the art that various modifications and variations can be made in the present disclosure without departing from the scope of the disclosure. For instance, features illustrated or described as part of one embodiment can be used with another embodiment to yield a still further embodiment. Thus, it is intended that the present disclosure covers such modifications and variations as come within the scope of the appended claims and their equivalents. As used herein, the term "or" is generally intended to be inclusive (i.e., "A or B" is intended to mean "A or B or both"). The terms "first," "second," and "third" may be used interchangeably to distinguish one component from another and are not intended to signify location or importance of the individual components.

Throughout the specification, and in the claims, the term "connected" means a direct electrical, mechanical, or magnetic connection between the things that are connected, without any intermediary devices. The terms "coupled" or "integrated" mean either a direct electrical, mechanical, or magnetic connection between the things that are connected or an indirect connection through one or more passive or active intermediary devices. The term "circuit," "module," or "mechanism" may refer to one or more passive and/or active components that are arranged to cooperate with one another to provide a desired function.

The terms "substantially," "close," "approximately," "near," and "about" generally refer to being within +/−10% of a target value. Unless otherwise specified the use of the ordinal adjectives "first," "second," and "third," etc., to describe a common object, merely indicate that different instances of like objects are being referred to and are not intended to imply that the objects so described must be in a given sequence, either temporally, spatially, in ranking, or in any other manner.

It is to be understood that the terms so used are interchangeable under appropriate circumstances such that the embodiments of the disclosure described herein are, for example, capable of operation in other orientations than those illustrated or otherwise described herein.

The terms "left," "right," "front," "back," "top," "bottom," "over," "under," and the like in the description and in the claims, if any, are used for descriptive purposes and not necessarily for describing permanent relative positions.

As described herein, embodiment of the present disclosure provides systems and methods related to instruments or tools used in performing surgery on a patient and, more particularly, to a peristaltic pump attachment for suction and irrigation during electrosurgical procedures.

FIG. 1 depicts a front view illustrating an embodiment of a system according to the present disclosure including an example electrosurgical unit in combination with a fluid source, an example handheld electrosurgical device and a peristaltic pump utilizing a hybrid peristaltic pump attachment, according to embodiments. The system 100 may be carried on a movable or portable hand cart 102 having a support structure 104 comprising a hollow (or solid) cylindrical post which includes a platform 106. The platform 106 including a pedestal table to provide a flat, stable surface allowing an electrosurgical unit 110 to rest. The hand cart 102 may include a pole 108 having an adjustable height by sliding the pole 108 up or down. A fluid source 120 may be supported at the top of the pole 108, but not limited thereto.

The fluid source 120 may comprise a bag or other container from which fluid 112 may flow through irrigation tubing 116 and to an electrosurgical device 130, which may be dispensable therefrom. In embodiments, a drip chamber 114 may be utilized between the fluid source 120 and the electrosurgical device 130. In embodiments, the fluid 112 may include saline and may include physiologic saline such as sodium chloride (NaCl) 0.9% weight/volume solution. Saline, an electrically conductive fluid, and other suitable electrically conductive fluids may be used. In embodiments, the fluid may include a nonconductive fluid, such as deionized water, which may still provide advantages over using no fluid and may support cooling of portions of electrosurgical device 130 and tissue or reducing the occurrence of tissue sticking to the electrosurgical device 130.

In embodiments, the irrigation tubing 116 may flow through pump 122 to convey fluid to the electrosurgical device 130 and control fluid flow. In embodiments, the pump 122 may be a peristaltic pump such as a rotary peristaltic pump. The peristaltic pump may convey the fluid through the irrigation tubing 116 by way of intermittent forces placed on the external surface of the delivery tubing. Peristaltic pumps are often applied during operation of the electrosurgical device 130 because the mechanical elements of the pump places forces on the external surface of the delivery tubing and do not come into direct contact with the fluid, which can reduce the likelihood of fluid contamination.

In embodiments, a suction tubing 142 may flow through pump 122 to suction remnants (e.g., excess fluid, blood, tissue, byproducts, etc.) into the electrosurgical device 130 at a treatment area (not shown) during operation of the electrosurgical device 130 and control flow. In embodiments, the remnants may flow through the suction tubing 142, through pump 122 and into a waste container/receptacle 140.

Figure 3:
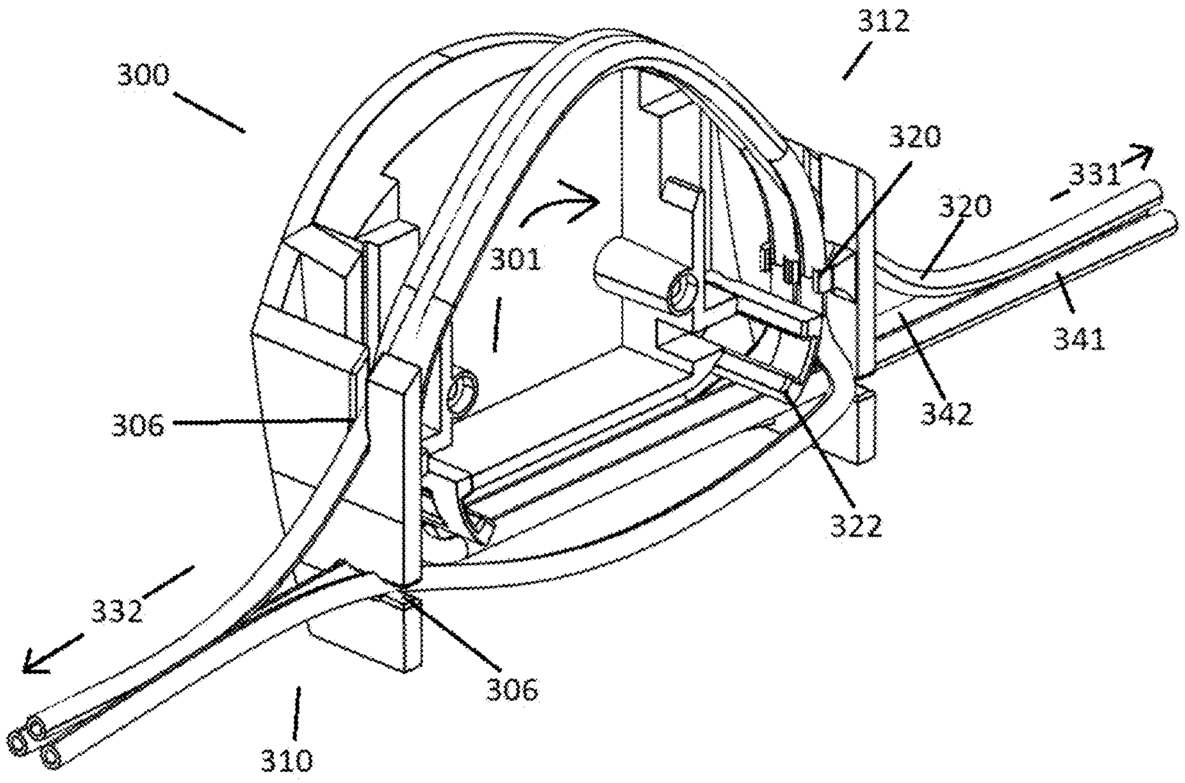
FIG. 3 depicts a hybrid peristaltic pump attachment to be integrated with a peristaltic pump, according to embodiments.
Figure 4:
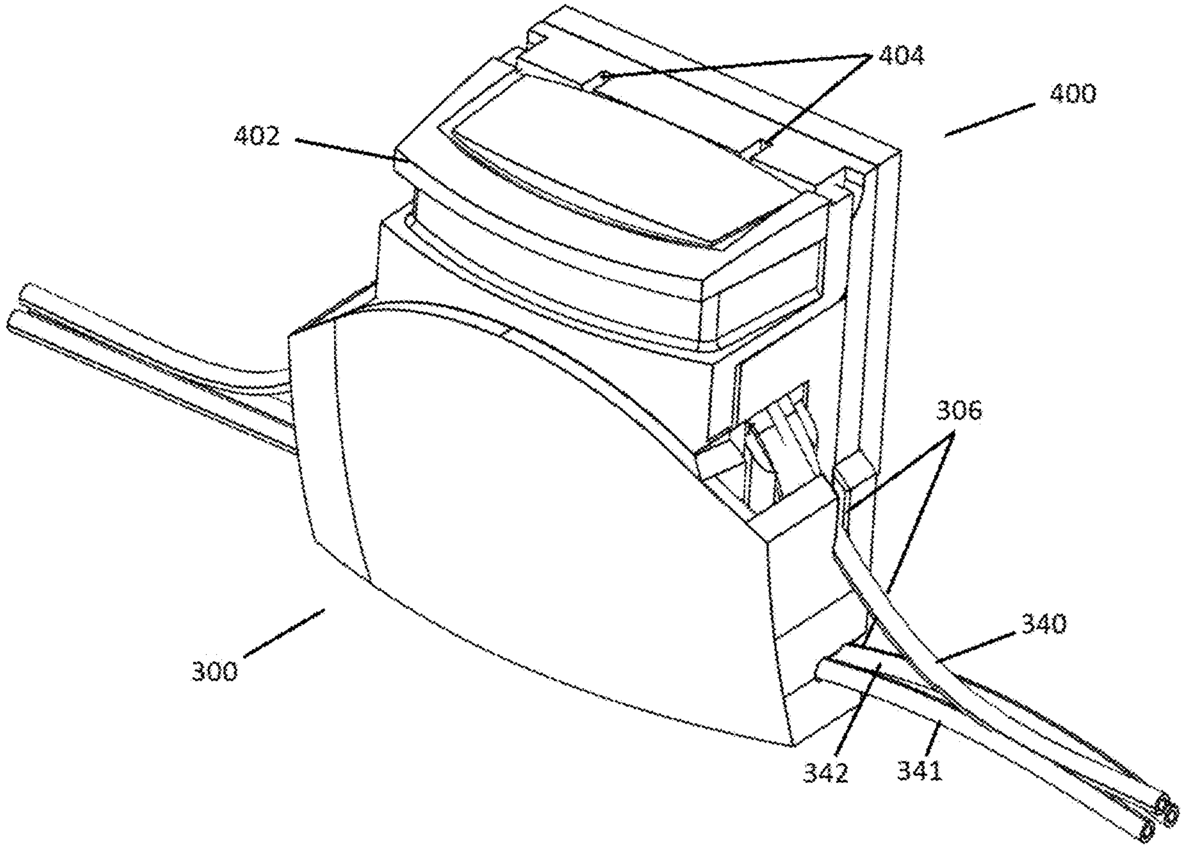
FIG. 4 depicts a hybrid peristaltic pump attachment integrated with a peristaltic pump, according to embodiments.
Figure 5:
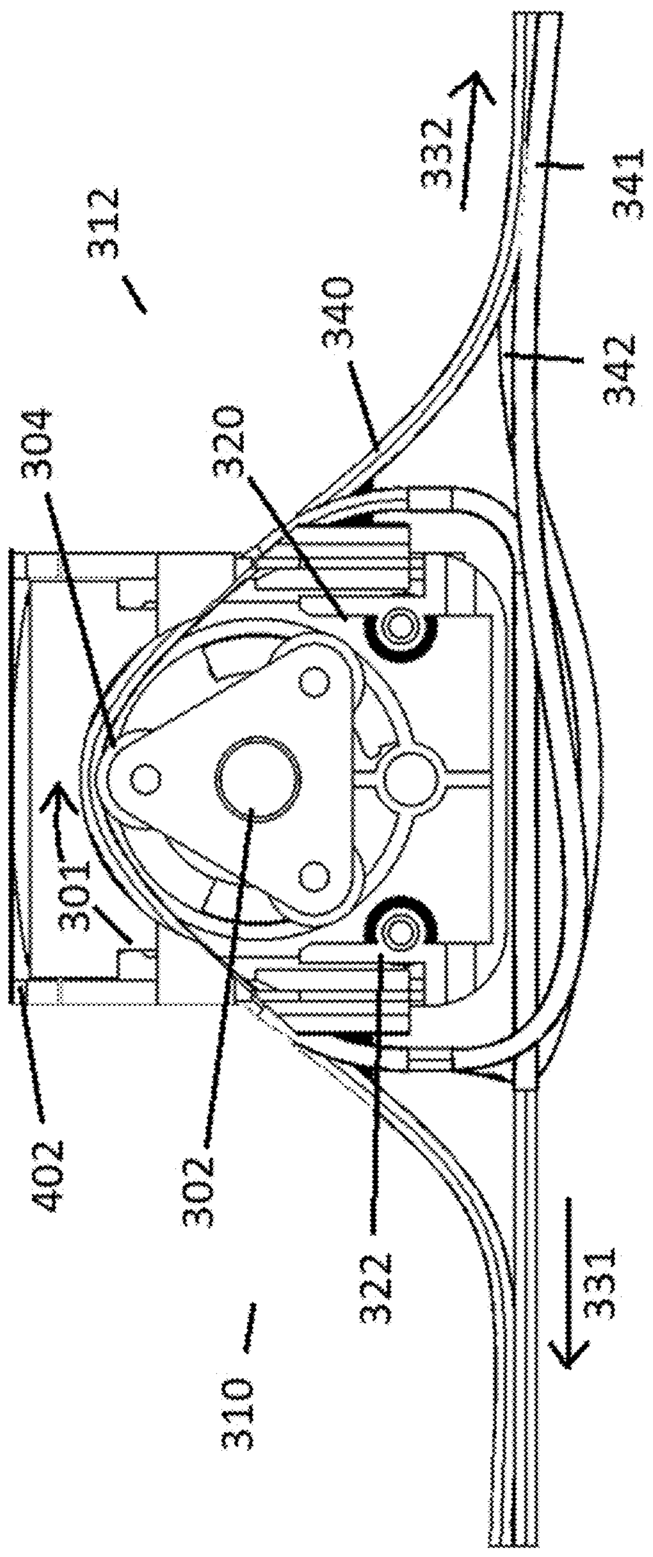
FIG. 5 depicts a cross-sectional view of a hybrid peristaltic pump attachment integrated with a peristaltic pump, according to embodiments.

In embodiments, a hybrid peristaltic pump attachment 124 may be integrated with the pump 122 such that the irrigation tubing 116 and suction tubing 142 may be individually oriented within the hybrid peristaltic pump attachment 124 and encompass the pumping mechanisms of the peristaltic pump 122 (referring to FIGS. 3-5). In embodiments, based on the orientation of each tube, simultaneous irrigation of fluid 112 through the irrigation tubing 116 and suction of remnants through the fluid suction tubing 142 during operation of the electrosurgical device 130 may be realized, even though the pumping mechanisms of pump 122 may only operate/rotate in one direction at a time. While a single irrigation tube and a single suction tube may be depicted, the foregoing is illustrative of various example embodiments and is not to be construed as limiting thereof.

In embodiments, the example electrosurgical unit 110 may provide at least one or more monopolar RF power outputs to a specified electrosurgical instrument such as electrosurgical device 130. In one example, the electrosurgical unit 110 can be used for delivery of RF energy to instruments indicated for cutting and coagulation of soft tissue and for delivery of RF energy concurrent with fluid to instruments indicated for hemostatic sealing and coagulation of soft tissue and bone.

In embodiments, the electrosurgical device 130 may be connected to the electrosurgical unit 110 via cable 126. The cable 126 may include plugs 134 that connect with receptacles 136 on the electrosurgical unit 110. In embodiments, a receptacle may correspond with an active electrode receptacle and one or more receptacles can correspond with controls on the electrosurgical device 130. In embodiments, a receptacle can correspond with a second active electrode receptacle. An additional cable may connect a ground pad electrode to a ground pad receptacle of the electrosurgical unit 110.

The features of electrosurgical unit 110 described are for illustration, and the electrosurgical units suitable for use with device 130 may include some, all, or other features than those described below. In one example, the electrosurgical unit 110 is capable of operating in at least monopolar mode as well as multiple functions within the monopolar mode such as a monopolar cutting function, a monopolar coagulation function, and monopolar hemostasis or tissue sealing function. In the monopolar cutting function, monopolar RF energy is provided to the device 130 at a first power level and/or a first waveform (collectively first or cutting RF energy setting). For example, cutting RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS). In the monopolar coagulation function, monopolar RF is energy is provided to the electrode at a second power level and/or second waveform (collectively second, or coagulating RF energy setting) that is different than at least one of the first power level or the first waveform. For example, coagulating RF energy for a coagulation function may be provided at a relatively higher voltage than the cut voltage and with a pulsed current, such as 1% to 6% on and 99% to 94% off, respectively (or 1% to 6% duty cycle). Other duty cycles are contemplated. The electrosurgical unit 110 may provide monopolar RF energy at a third power level and/or third waveform (collectively third, or hemostatic sealing RF energy setting) along with fluid for a (generally low voltage) hemostasis or tissue sealing function that may be the same as or different than the cutting and coagulating RF settings provided to the device 130 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In embodiments, the electrosurgical unit 110 provides RF energy to the active electrode as a signal having a frequency in the range of 100 KHz to 10 MHZ. Typically, this energy is applied in the form of bursts of pulses. Each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes.

The electrical surgical unit 110 may include a power switch to turn the unit on and off and an RF power setting display to display the RF power supplied to the electrosurgical device 130. The power setting display can display the RF power setting numerically in a selected unit such as watts.

In embodiments, electrosurgical unit 110 may include an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector corresponding with each of the different monopolar settings used in the different functions.

In embodiments, electrosurgical unit 110 may also include a fluid flow rate setting display and flow rate setting selector. The display can include indicator lights, and the flow rate selector can include switches. Pushing one of the flow rate switches selects a fluid flow rate, which is then indicated in display.

While not being bound to a particular theory, the relationship between the variables of fluid flow rate Q (such as in units of cubic centimeters per minute (cc/min)) and RF power setting Ps (such as in units of watts) can be configured to inhibit undesired effects such as tissue desiccation, electrode sticking, smoke production, char formation, and other effects while not providing a fluid flow rate Q at a corresponding RF power setting Ps not so great as to disperse too much electricity and or overly cool the tissue at the electrode/tissue interface. In embodiments, the electrosurgical unit 110 may be configured to increase the fluid flow rate Q generally linearly with an increasing RF power setting Ps for each of the fluid flow rate settings (e.g., low, medium, and high).

In embodiments, the electrosurgical unit 110 may be configured to include control of the pump 122. In embodiments, the speed of the pump 122, fluid irrigation, and fluid suction may be predetermined based on input variables such as the RF power setting and the fluid flow rate setting. In one example, the pump 122 can be integrated with the electrosurgical unit 110.

While the electrosurgical device 130 is described with reference to the electrosurgical unit 110 and other elements of system 100, it should be understood the description of the combination is for the purposes of illustrating system 100. It may be possible to use the hybrid peristaltic pump attachment in other systems utilizing peristaltic pumps.

Figure 2:
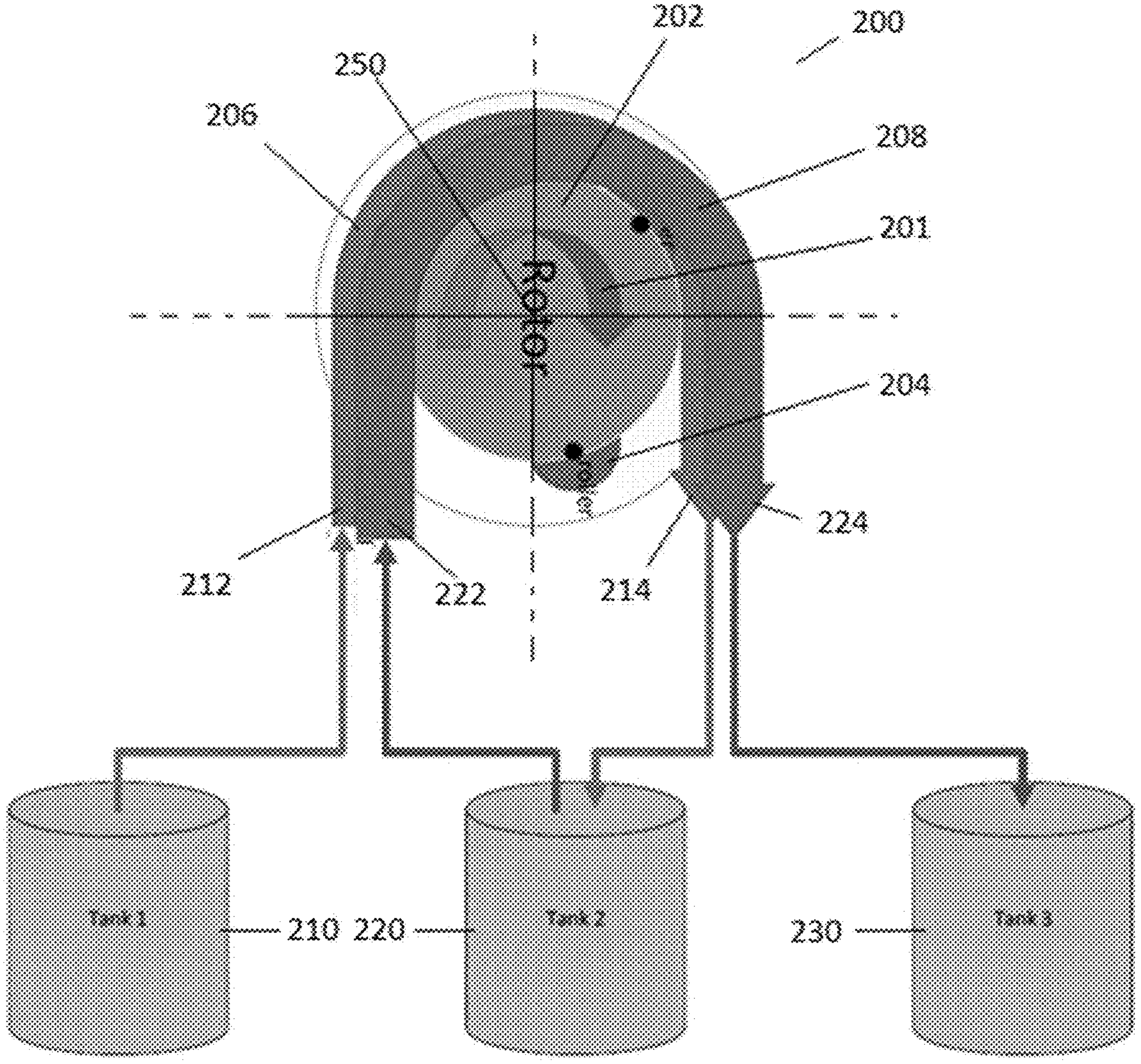
FIG. 2 depicts a conceptual view of a peristaltic pump, according to embodiments.

With reference to FIG. 2, a peristaltic pump 200 may include mechanisms such as a rotor 202, one or more rollers 204, and a tube channel (not depicted) to hold or accept tube(s). A first flexible tube 206 may be attached, at least partially surrounding the pump 200 within in the tube channel so the rollers 204 may roll over the tube by the rotation 201 of the rotor 204 about an axis 250 and the fluid inside the first flexible tube 206 moves with the direction of the rotation 201. In embodiments, some pumps come with the flexible tube already installed and some require the placement of the tube inside the pump, via an attachment. For those with the tube already placed inside the pump, it is important to connect the source and destination of the fluid to the correct port and for the others, it is important to place the tube in the correct orientation inside the pump because the fluid will only travel in a single direction according to the rotation of the rotor. In embodiments, the fluid pumping rate may depend on multiple parameters such as the diameter of the tube, rotor speed, roller size and depth of tube compression, etc.

In embodiments, an additional, second flexible tube 208 may be integrated near the first flexible tube 206. The fluid pumping concept will not change as described using a first flexible tube 206, and the fluid direction may still be in the same direction 201 as previously mentioned with the first flexible tube 206 (i.e., the direction of fluid flow is dependent on the rotation of the rotor). In embodiments, the rotor 204 may be driven, by a motor (not shown) with sufficient power, such that the pumping rate per tube will not change regardless of the number of tubes. In embodiments, the flexible tube 206 may comprise an input port 212 and an output port 212 and the flexible tube 208 may comprise an input port 222 and an output port 224. Input port 212 may be connected to a first unit (e.g., a fluid source as depicted in FIG. 1). Input port 222 and output port 212 may be connected to/integrated with a second unit 220 (e.g., an electrosurgical device) and output unit 224 may be connected to yet a third unit 230 (e.g., a waste containment unit).

Unlike conventional peristaltic pump systems, the flexible tubes 206 and 208 may be individually and strategically orientated/routed within the hybrid pump attachment such that upon attaching the hybrid pump attachment to the peristaltic pump, the flexible tubes 206 and 208 encase the rotor 202 and rollers 204 wherein the rollers 204 are aligned with the flexible tubes 206 and 208. In embodiments, the tubes 206 and 208 may be aligned with rollers 204 such that, during rotation of the rotor 202, the rollers 204 may convey the fluid (or other substances) through the flexible tubes 206 or 208 by way of intermittent forces placed on the external surface of the flexible tubes 206 or 208. In embodiments, based on the orientation of the plurality of tubes 206 and 208 within the hybrid pump attachment, individual configuration of fluid flow may be realized (i.e., each tube may be oriented such that either irrigation or suction may be realized, concurrently, while the rotor 202 rotates in a single direction 201).

Thus, as the rotor 202 rotates, the contents of the first unit 210 (e.g., fluid/saline/etc.) may flow from the first unit 210, via input port 212, to the second unit 220 (e.g., a treatment area for electrosurgical devices), via output port 214, with a fluid flow rate. Simultaneously, the contents of the second unit 220 (e.g., remnants such as excess fluid, blood, tissue, byproducts, etc. from a treatment area during operation of an electrosurgical device) may flow from the second unit 220, via input port 222, to the third unit 230, via output port 224, with the same fluid flow rate for containment/disposal. In embodiments, the same flow rate may be realized whether a single or multiple flexible tubes are used.

Thus, by utilizing specific arrangements for each tube within the hybrid pump attachment, each tube may be configured to irrigate or suction depending on when and where the rollers come into contact with each tube during rotor rotation. The bundling of one or more tubes within the hybrid pump attachment with strategically orientated directions provides an ease of integration with a peristaltic pump (i.e., tubes individually configurable to provide irrigation or suction) and provides single directional placement of the hybrid attachment on the side of the pump. Thus, prevention of potential mistakes in individual tube placement/linkage or flow direction may be realized. While two tubes may be depicted, the foregoing is illustrative of various example embodiments and is not to be construed as limiting thereof. The hybrid pump attachment may comprise three, four, or more tubes, each individually orientable to allow for irrigation or suction.

Peristaltic pumps, such as pump 200, that utilize a hybrid pump attachment according to an embodiment disclosed herein, may be retrofitted with hybrid pump attachment of one of the embodiments disclosed herein without modifying the pump rotor 202 or rollers 204. Thus, existing peristaltic pumps can beneficially use embodiments of the hybrid pump attachment disclosed herein. However, the peristaltic pump 300 may also be modified such that the pump cavity is deeper or wider in order to receive an embodiment of the hybrid pump attachment disclosed herein.

Note, various quantities, sizes and dimensions of tubes, rollers and rotors may be realized according to preferred fluid flow rate, volume, and the size of the overall pump. For example, smaller diameter tubes may increase flow rate, while larger diameter tubes may decrease fluid flow rate. In addition to or alternatively, increasing the rotational speed of the rotor may increase the fluid flow rate and, thus, increase the volume of fluid irrigated/suctioned.

Referring to FIGS. 3-5, FIG. 3 depicts a hybrid pump attachment attachable to a peristaltic pump, according to embodiments. The hybrid pump attachment 300 may include an attachable/detachable casing to attach and detach to and from a peristaltic pump as provided herein (illustrated in FIG. 4). In embodiments, the hybrid pump attachment 300 may include a plurality of tube openings to receive and direct a plurality of flexible tubes 340-342. In embodiments, the flexible tubes 340-342 may be individually and strategically orientated/routed within the hybrid pump attachment, such that upon attaching the hybrid pump attachment to the peristaltic pump, the flexible tubes 340-342 encase a rotor (not shown) and rollers (not shown) wherein the rollers align with the flexible tubes 340-342. In embodiments, the rotor and the rollers may be position within the plurality of flexible tubes 340-342 such that, during rotation of the rotor, space between the tubes and the rotor/rollers are evenly distributed (i.e., 360°, evenly spaced rotation). In embodiments, the tubes 340-342 may be aligned with rollers such that, during rotation of the rotor, the rollers may convey the fluid (or other substances) through the flexible tubes 340-342 by way of intermittent forces placed on the external surface of the flexible tubes 340-342. In embodiments, based on the orientation of the plurality of flexible tubes 340-342 within the hybrid pump attachment, individual configuration of fluid flow may be realized (i.e., each tube may be oriented such that either irrigation or suction may be realized, concurrently, while the rotor rotates in a single direction).

In embodiments, flexible tube 340 may be a single irrigation line and may enter, via a first side 310, and exit, via a second side 312 (or vise-versa), through two of the plurality of tube holes 306 and be positioned near the top of the hybrid pump attachment such that, when the rotor rotates, rollers execute intermittent force on the external surface of the irrigation line 340. In embodiments, irrigation line 340 may receive only a portion of the potential intermittent force from the rollers, as irrigation line 340 may not encompass the entire rotor. Thus, as the rotor rotates in direction 301, the intermittent force from the rollers generates and directs fluid flow in direction 331 (e.g., irrigation flow).

In embodiments, flexible tubes 341 and 342 may be a first and a second suction line and may enter, via a first side 310, and exit, via a second side 312 (or vise-versa), through at least two alternative tube holes of the plurality of tube holes 306 and be positioned such that the tubes enter the first side 310, run through the hybrid pump attachment 300 (e.g., near the bottom portion) and as the first and second suction lines 341 and 342 approach the interior of the second side 312, the first and second suction lines 341 and 342 may loop around the a rotor of a peristaltic pump, and exit through at least one of the plurality of tube holes 306 of side 312. In embodiments, first and second suction lines 341 and 342 may completely encompass the rotor such that they receive approximately the full potential intermittent force from the rollers of the peristaltic pump. Thus, as the rotor rotates in direction 301, the intermittent force from the rollers generates and directs fluid flow of the first and second suction lines 341 and 342 in direction 332 (e.g., suction flow). Therefore, due to the individual orientation of each flexible tube looping around or surrounding the rotor, as the rotor rotates in a single direction 301, fluid flow may be generated both in sequence with the direction of the rotor (e.g., irrigation line 340/flow) and in the opposite direction (e.g., suction lines 341 and 342/flow) relative to the direction 301 of the rotor.

In embodiments, the flexible tubes that have been oriented to flow in direction 331 (e.g., irrigation line 340) may be grouped together and flexible tubes oriented to flow in direction 332 (e.g., first and second suction lines 341 and 342) may be grouped together (e.g., entering and exiting the same tube holes 306 or located together near entering/exiting sides 310 and 312). In embodiments, suction lines may be grouped together near the top portion and irrigation lines may be grouped together near the bottom portion when integrated into the hybrid pump attachment 300. Thus, when integrating with a peristaltic pump, flexible tubes 340-342 may be readily identified from an external view of the hybrid pump attachment 300 such that the irrigation or suction tubes may be easily identifiable. Thus, potential mistakes in tube placement/linkage between components and incorrect fluid flow may be prevented.

While three tubes may be depicted (one tube for irrigation and two tubes for suction), the foregoing is illustrative of various example embodiments and is not to be construed as limiting thereof. The hybrid pump attachment may comprise greater or fewer tubes, each individually orientable to allow for irrigation or suction between the same or multiple alternative locations.

In embodiments, a plurality of flexible tube grips 320 may be positioned on sides 310 and 312, internally, to secure the plurality of flexible tubes 340-342 from any erratic movement and any unintentional displacement during operation. In embodiments, attachable components 322 may be integrated within the hybrid pump attachment 300 and structurally integrated with the interior sides to further secure and protect the flexible tubes 340-342. The attachable components 322 may aid in the structural support of the hybrid pump attachment and may further provide additional attachment mechanisms to allow integration with the peristaltic pump.

FIG. 4 depicts a hybrid peristaltic pump attachment integrated with a peristaltic pump, according to embodiments. In embodiments, a hybrid peristaltic pump attachment 300 may be integrated with a peristaltic pump 400 as described herein. Lid 402 of the peristaltic pump 400 may be opened, rotatable from a horizontal position to a vertical position, via hinges 404 and configured to receive the hybrid peristaltic pump attachment 300. In embodiments, the peristaltic pump 400 may receive the hybrid peristaltic pump attachment 300 by clipping, locking, or otherwise accepting the hybrid peristaltic pump attachment 300. In embodiments, the peristaltic pump 400 may be pre-configured with various indentations, groves or otherwise structurally configured to readily place, slid, or clip onto the hybrid peristaltic pump attachment 300. Thus, due to the configuration of the hybrid peristaltic pump attachment 300, the hybrid peristaltic pump attachment 300 may only be incorporated with the peristaltic pump 400 in a single orientation as depicted (i.e., the hybrid peristaltic pump attachment 300 may not be rotatably integrated (e.g., such as rotating the hybrid peristaltic pump attachment 300 clockwise/counter-clockwise in a 90°, 180°, 270°, etc. direction) onto the peristaltic pump 400. Such ease of integration with the peristaltic pump 400 prevents potential mistakes in tube placement/linkage between components and incorrect fluid flow.

In embodiments, as described herein, the hybrid peristaltic pump attachment 300 may be integrated with the peristaltic pump 400 such that the irrigation tubing 340 and suction tubing 341 and 342 may be individually oriented within the hybrid peristaltic pump attachment 300 and encompass the pumping mechanisms (referring to FIG. 5) of the peristaltic pump 400. In embodiments, based on the orientation of each flexible tube, simultaneous irrigation of fluid through the irrigation tubing 340 and suction of remnants through the first and second suction lines 341 and 342, during operation of an electrosurgical device may be realized. Even though the pumping mechanisms of the peristaltic pump 400 may only operate/rotate in one direction at a time, irrigation and suction may be simultaneously realized due to the differing orientations of the flexible tubes 340-342 within the hybrid peristaltic pump attachment 300. While a single irrigation line and two suction lines may be depicted, the foregoing is illustrative of various example embodiments and is not to be construed as limiting thereof.

In embodiments, once the hybrid peristaltic pump attachment 300 has been integrated into the peristaltic pump 400. Lid 402 may be closed, rotatable back to the horizontal position from the vertical position, via hinges 404 and configured to hold the hybrid peristaltic pump attachment 300 in place.

FIG. 5 depicts a cross-sectional view of a hybrid peristaltic pump attachment integrated with a peristaltic pump, according to embodiments. In embodiments, the flexible tubes 340-342 may be individually and strategically oriented/routed within the hybrid pump attachment, such that upon attaching the hybrid pump attachment to the peristaltic pump, the flexible tubes 340-342 encase a rotor 302 and rollers 304 wherein the rollers align with the flexible tubes 340-342. In embodiments, the rotor 302 and the rollers 304 may be position within the plurality of flexible tubes 340-342 such that, during rotation of the rotor 302, space between the tubes and the rotor 302/rollers 304 are evenly distributed (i.e., 360°), evenly spaced rotation). In embodiments, the tubes 340-342 may be aligned with rollers 304 such that, during rotation of the rotor 302 in direction 301, the rollers 304 may convey the fluid (or other substances) through the flexible tubes 340-342 by way of intermittent forces placed on the external surface of the flexible tubes 340-342. In embodiments, based on the orientation of the plurality of flexible tubes 340-342 within the hybrid pump attachment, individual configuration of fluid flow may be realized (i.e., each tube may be oriented such that either irrigation or suction may be realized, concurrently, while the rotor rotates in a single direction).

In embodiments, flexible tube 340 may be a single irrigation line and may enter, via a first side 310, and exit, via a second side 312 (or vise-versa), through two of the plurality of tube holes 306 and be positioned near the top of the hybrid pump attachment such that, when the rotor 302 rotates, rollers execute intermittent force on the external surface of the irrigation line 340. In embodiments, irrigation line 340 may receive at least a portion of the potential intermittent force from the rollers 304, as irrigation line 340 may not encompass or completely loop around the entire rotor 302. Thus, as the rotor 302 rotates in direction 301, the intermittent force from the rollers generates and directs fluid flow in direction 331 (e.g., irrigation flow).

In embodiments, flexible tubes 341 and 342 may be a first and a second suction line and may enter, via a first side 310, and exit, via a second side 312 (or vise-versa), through at least two alternative tube holes of the plurality of tube holes 306 and be positioned such that the tubes enter the first side 310, runs through the hybrid pump attachment 300 (e.g., near the bottom portion) and as the first and second suction lines 341 and 342 approach the interior of the second side 312, the first and second suction lines 341 and 342 may loop around the a rotor of a peristaltic pump, and exit through at least one of the plurality of tube holes 306 of side 312. In embodiments, first and second suction lines 341 and 342 may completely encompass the rotor such that they receive approximately the full potential intermittent force, are at least a portion thereof, from the rollers of the peristaltic pump. Thus, as the rotor rotates in direction 301, the intermittent force from the rollers generates and directs fluid flow of the first and second suction lines 341 and 342 in direction 332 (e.g., suction flow).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features: rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A system for electrosurgical treatment comprising:

an electrosurgical device configured to provide electrosurgical treatment to a tissue area;

a peristaltic pump including a rotor and a plurality of rollers, wherein the rotor and the plurality of rollers have a central axis;

a housing releasably coupleable to the peristaltic pump, the housing including a plurality of flexible tubes fluidly connectable to the electrosurgical device, wherein the plurality of flexible tubes is orientated within the housing such that when the housing is coupled to the peristaltic pump, the plurality of flexible tubes at least partially surrounds the rotor and the plurality of rollers, wherein the plurality of rollers aligns with the plurality of tubes; and the rotor rotatable about the central axis, wherein the plurality of rollers conveys fluid through the plurality of flexible tubes by way of applying intermittent forces on the external surface of the plurality of flexible tubes, wherein at least a first tube of the plurality of tubes conveys a first fluid to a first location and at least a second tube of the plurality of tubes conveys a second fluid to a second location, wherein one of the plurality of flexible tubes is arranged so as to encircle the rotor.

2. The system of claim 1, wherein at least the first tube irrigates an electrically conductive fluid to the tissue area and at least the second tube suctions remnants from the tissue area during the electrosurgical treatment while maintaining the same axial rotor rotation.

3. The system of claim 2, wherein the remnants include one or more of excess electrically conductive fluid, blood, or tissue.

4. The system of claim 1, wherein the electrosurgical treatment includes treating the tissue area with radiofrequency (RF) electrical energy of the electrosurgical device, treating the tissue area with an electrically conducive fluid, conveyed through the first tube and suctioning remnants from the tissue area through the second tube.

5. The system of claim 1, wherein the fluid conveyed through the plurality of flexible tubes each have equivalent volumetric flow rates.

6. The system of claim 1, wherein the housing is readily integrated with the peristaltic pump while maintaining rotation about the axis.

7. The system of claim 1, wherein each flexible tube is individually oriented within the hybrid pump attachment and routes flow to and from distinct sources and destinations.

8. A hybrid pump attachment comprising:

a casing configured to be releasably coupleable to a peristaltic pump, the casing including a plurality of apertures configured to allow the passage therethrough of flexible tubes;

the plurality of flexible tubes orientated within the casing and fluidly attachable to at least one of a fluid source, an electrosurgical device, and a waste destination, wherein a plurality of rollers integrated with the peristaltic pump conveys fluid through the plurality of flexible tubes by way of applying intermittent forces on the external surface of the plurality of flexible tubes as the plurality of rollers rotate about an axis within the peristaltic pump, wherein at least a first tube of the plurality of flexible tubes conveys a first fluid to a first location and at least a second tube of the plurality of flexible tubes conveys a second fluid to a second location, wherein one of the plurality of flexible tubes is arranged so as to encircle the plurality of rotors.

9. The system of claim 8, wherein the first tube is an electrically conductive tube and is conveyed to a tissue area being treated by an electrosurgical device and the second fluid is suctioned remnants from the tissue area during the electrosurgical treatment.

10. The system of claim 9, wherein the remnants include one or more of excess electrically conductive fluid, blood, or tissue.

11. The system of claim 8, wherein the fluid conveyed through the plurality of flexible tubes each have equivalent volumetric flow rates.

12. The system of claim 8, wherein each flexible tube is individually oriented within the casing, wherein each flexible tube routes fluid to distinct destinations and from distinct sources while maintaining rotation about the axis.

13. A method for use with an electrosurgical device, the method comprising:

coupling a housing to a peristaltic pump, the housing including a plurality of flexible tubes fluidly connectable to an electrosurgical device, wherein the plurality of flexible tubes is orientated within the housing such that when the housing is coupled to the peristaltic pump the plurality of flexible tubes at least partially surrounds a rotor of the peristaltic pump and one of the plurality of flexible tubes is arranged so as to encircle the rotor providing an electrosurgical treatment to a tissue area via the electrosurgical device coupled to the peristaltic pump;

irrigating, through a first of the plurality flexible tubes, a first fluid from a source and applying the first fluid to the tissue area with the electrosurgical device during the electrosurgical treatment; and suctioning, through a second of the plurality of flexible tubes, a second fluid from the tissue area to a target destination with the electrosurgical device.

14. The method of claim 13, further comprising providing the electrosurgical treatment, irrigating the first fluid, and suctioning the second fluid simultaneously.

15. The method of claim 13, further comprising providing the electrosurgical treatment includes treating the tissue area with radiofrequency (RF) electrical energy.

16. The method of claim 13, further comprising irrigating the first fluid includes irrigation of an electrically conductive fluid and suctioning the second fluid includes suctioning remnants resulting from the electrosurgical treatment.

17. The method of claim 16, wherein the remnants include one or more of excess electrically conductive fluid, blood, or tissue.

18. The method of claim 13, further comprising irrigating the first fluid and suctioning the second fluid at a same volumetric flow rate.

* * * * *